(12) United States Patent
Wesse

(10) Patent No.: US 8,233,966 B2
(45) Date of Patent: Jul. 31, 2012

(54) METHOD AND X-RAY DIAGNOSTIC DEVICE FOR GENERATION OF AN IMAGE OF A MOVING BODY REGION OF A LIVING SUBJECT

(75) Inventor: Florian Wesse, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1257 days.

(21) Appl. No.: 11/489,291

(22) Filed: Jul. 18, 2006

(65) Prior Publication Data

US 2007/0027389 A1 Feb. 1, 2007

(30) Foreign Application Priority Data

Jul. 18, 2005 (DE) .......................... 10 2005 033 471

(51) Int. Cl.
*A61B 5/05* (2006.01)
(52) U.S. Cl. ........ 600/428; 600/425; 600/427; 600/534; 378/62; 378/69
(58) Field of Classification Search .................. 600/425, 600/427–429, 529, 534; 378/4, 41, 62, 69, 378/101, 109–112, 8
See application file for complete search history.

(56) References Cited

U.S. PATENT DOCUMENTS

| | | | |
|---|---|---|---|
| 6,298,260 B1 | 10/2001 | Sontag et al. | |
| 6,633,775 B1 | 10/2003 | Bernard | |
| 7,769,430 B2 * | 8/2010 | Mostafavi | ..................... 600/428 |
| 2003/0152189 A1 | 8/2003 | Li et al. | |
| 2005/0113673 A1 * | 5/2005 | Avinash et al. | ............... 600/413 |
| 2006/0074300 A1 | 4/2006 | Green | |

FOREIGN PATENT DOCUMENTS

WO WO 2004062501 A2 * 7/2004

* cited by examiner

*Primary Examiner* — Brian Casler
*Assistant Examiner* — Daniel Huntley
(74) *Attorney, Agent, or Firm* — Schiff Hardin LLP

(57) ABSTRACT

In a method and an x-ray diagnostic device for generation of an image of a body region of a living subject that executes a movement due to respiration, respiration signals of the subject are acquired and x-ray projections of the subject are acquired from different projection directions. The intensity of the x-ray radiation emanating from an x-ray source in the acquisition of the x-ray projections is modulated such that the intensity assumes a desired value, or a value decreased relative to the value, dependent on the value of the amplitude of the respiration signal and/or the respiration position of the subject.

21 Claims, 7 Drawing Sheets

METHOD AND X-RAY DIAGNOSTIC DEVICE FOR GENERATION OF AN IMAGE OF A MOVING BODY REGION OF A LIVING SUBJECT

BACKGROUND OF THE INVENTION

1. Field of the Invention

The present invention concerns a method and an x-ray diagnostic device for generation of an image of a moving body region of a living subject that executes a movement due to respiration. X-ray projections of the body region of the subject, from which images of the subject are reconstructed with a computer, are acquired from different projection directions with a radiological measurement system that has an x-ray source and an x-ray detector.

2. Description of the Prior Art

In the generation of images of a body region of a living subject that executes a movement due to respiration, the desire frequently exists to generate images of the body region of the subject only in a specific phase of the respiration cycle. For example, it is known from U.S. Pat. No. 6,633,775 to synchronize the acquisition of an x-ray exposure with the respiration of a patient. For this purpose, the respiration cycle of the patient is detected and an x-ray exposure of the body part of the patient to be imaged is acquired at a specific degree of the inhalation of the patient.

In the acquisition of x-ray projections of a body region of a patient from various projection directions in x-ray computed tomography, for example with an x-ray computed tomography apparatus of the third generation in which a measurement system with an x-ray source and an x-ray detector rotates continuously around the patient, it is known to record the respiration cycle of the patient in parallel with the acquisition of the x-ray projections. The acquisition of the x-ray projections can thereby ensue during continuous table feed, i.e., continuous displacement of the patient on a patient table relative to a measurement system (spiral mode) or given a fixed position of the patient positioning table (sequence mode). Through the parallel recording of the respiration cycle of the patient, images of the body region of the patient can be specifically reconstructed in connection with the acquisition of the x-ray projections at selected phases of the respiration cycle of the patient. This method has the disadvantage that the patient is also exposed to x-ray radiation at the points in time of the respiration cycle of the patient at which no image information of the body region of the patient is required or, respectively, desired.

SUMMARY OF THE INVENTION

An object of the present invention is to provide a method and an x-ray diagnostic device of the aforementioned type wherein the x-ray dose, to which the subject is exposed, in order to generate an image of a body region of the subject that executes a movement due to respiration, is reduced.

This object is achieved in accordance with the invention by a method in which respiration signals of the subject are determined with a device for acquisition of respiration signals, and at the same time x-ray projections of the body region of the subject are acquired from different projection directions, with the intensity of the x-ray radiation emanating from the x-ray source being modulated for the acquisition of the x-ray projections such that the intensity for the acquisition of a projection assumes a desired value (or a value decreased relative to the desired value) dependent on the value of the amplitude of the current measured respiration signal and/or the current measured respiration position of the subject. The value or values of the amplitudes of the respiration signals, or the respiration position(s) at which the intensity should assume the desired value, thus can be predetermined, adapted to the particular patient. According to the invention, the subject is exposed to x-ray radiation with an intensity with which qualitatively high-grade images of the body region can be reconstructed only at the phase of the respiration cycle and/or the respiration position of the subject at which one or more images of the body region of the subject should be reconstructed. During the remaining time of the respiration cycle, the intensity is not decreased to zero, but rather to a predeterminable value so that further x-ray projections of the subject are in fact acquired from different directions, but with reduced intensity of the x-ray radiation. The inventive method has the consequence that the subject is exposed overall to a lower x-ray dose for generation of an image of the body region than is the case in conventional methods. The x-ray radiation is deliberately not completely deactivated in the phases of the respiration cycle at which no images should actually be generated since, in the case of given errors in the acquisition of x-ray projections with high intensity, x-ray projections acquired in these other phases can be necessary in order to be able to actually reconstruct an image of the body region of the subject. A safety aspect is thus present in the retention of the x-ray radiation with lower intensity in order to be able to use the x-ray projections acquired with lower intensity as supplementary x-ray projections for the reconstruction in the event of errors in the individual x-ray projections.

In an embodiment of the invention, the intensity of the x-ray radiation has the desired value when the ratio of the value of the amplitude of a currently-measured respiration signal to the value of the last-measured amplitude maximum is greater than or equal to or less than or equal to, at least one predetermined limit value. The intensity is accordingly modulated dependent on the ratio of the value of the amplitude of a currently-measured respiration signal to the value of the previously-measured amplitude maximum. Two different limit values are advantageously used in order to adjust the desired value of the intensity in a specific phase of the respiration cycle of the subject. Since the respiration cycle of the subject is normally not exactly periodical, it follows from this that the adjustment of the desired value for the intensity (which concerns the point in time and the duration of the adjustment) also does not ensue exactly periodically, but rather is precisely matched to the respiration cycle of the subject under examination.

In a further embodiment of the invention the intensity of the x-ray radiation assumes the desired value when the ratio of the value of the amplitude of a currently-measured respiration signal to a comparison value determined based on an amplitude maxima of a number of respiration cycles, is greater than or equal to, or less than or equal to, at least one predetermined limit value. In this case, the reference value is not the value of the last measured amplitude maximum. Rather, for a prospective consideration, for example, a number of amplitude maxima of a number of respiration cycles are averaged, or a median filter is also applied in order to obtain the comparison value. This is particularly advisable when a specific phase of the respiration cycle in the inhalation should be selected for the desired value of the intensity, in which specific phase of the respiration cycle x-ray projections with high intensity should be acquired. In this case, the reference variable (namely the value of the amplitude maximum of the current respiration cycle) does not even exist for the current respiration cycle.

According to another variant of the invention, the intensity of the x-ray radiation assumes the desired value during the entire phase of the inhalation or during the entire phase of the exhalation. This variant of the invention is advantageous when an image of the body region of the subject should be generated during the phase of the inhalation or during the phase of the exhalation.

In a further embodiment of the invention, the intensity of the x-ray radiation assumes the desired value when, during the phase of the exhalation, the ratio of the value of the amplitude of a currently-measured respiration signal to the value of the last-measured amplitude maximum or to a comparison value determined based on amplitude maximums of a number of respiration cycles, is smaller than or equal to a first predetermined limit value and greater than or equal to a second predetermined limit value. The intensity of the x-ray radiation can be modulated in a corresponding manner such that the intensity of the x-ray radiation assumes the desired value when, during the phase of the inhalation, the ratio of the value of the amplitude of a currently-measured respiration signal to the value of the last-measured amplitude maximum or to a comparison value determined based on amplitude maxima of a number of respiration cycles, is greater than or equal to a first predetermined limit value and less than or equal to a second predetermined limit value. A respiration interval of the respiration cycle is selected during the exhalation in the first embodiment for acquisition of x-ray projections of the body region of the subject with high intensity, but in the second embodiment a respiration interval of the respiration cycle of the subject is selected during the inhalation in order to generate targeted images of the body region as a basis of a subsequent diagnostic.

In a further embodiment of the invention, the intensity of the x-ray radiation assumes the desired value when the value of the amplitude of the currently-measured respiration signal is located between a fixed, predetermined, lower absolute amplitude limit value and a fixed, predetermined, upper absolute limit value. In this variant of the invention, no x-ray exposures of the body region of the subject are acquired with high intensity of the x-ray radiation at phase of the respiration cycle in which the values of the amplitudes of the respiration signal are relatively large or small.

In another embodiment of the invention provide that the absolute amplitude limit values for the subject are established using previously-measured values of the amplitudes of the respiration signals of the subject, and the intensity of the x-ray radiation only assumes the desired value only when the subject is located in the phase of the inhalation or the phase of the exhalation.

The respiration signal is preferably measured continuously, for which known devices (such as a respiration belt, a nasal cannula or a video or laser system for recording of the respiration signals) can be used.

The x-ray diagnostic apparatus is preferably a computed tomography apparatus, the x-ray source and x-ray detector of which continuously rotate around the subject during the acquisition of the x-ray projections. The x-ray diagnostic apparatus also can be a C-arm x-ray apparatus in which x-ray projections are only acquired at specific phases of the respiration cycle of the subject for acquisition of x-ray projections for the reconstruction of 3D images of the body region of the subject.

In a particularly preferred embodiment of the invention, for generation of the image, essentially only such x-ray projections are used that were acquired during the presence of the desired value of the intensity of the x-ray radiation.

The above object also is achieved by an x-ray diagnostic device having a computer that is programmed for execution of any of the embodiments of the method described above.

The x-ray diagnostic device can include an input unit for input of the desired value of the intensity, the value of the intensity decreased relative to the desired value, as well as for input of any type of limit values.

As already mentioned, the x-ray diagnostic apparatus can be a computed tomography apparatus or a C-arm x-ray apparatus.

DESCRIPTION OF THE PREFERRED EMBODIMENTS

Figure 1:
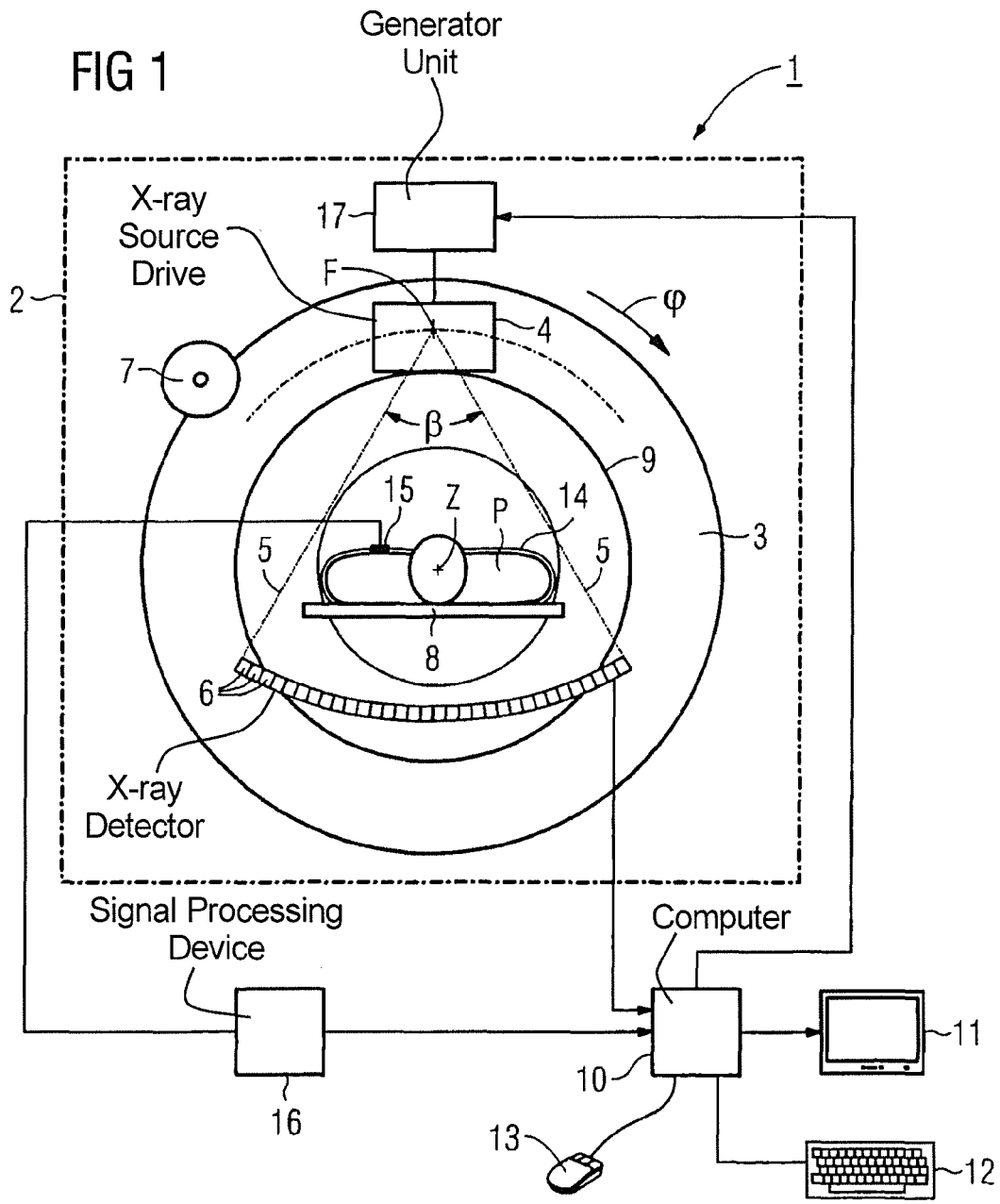
FIG. 1 shows an x-ray diagnostic device for implementation of the inventive method.

In the exemplary embodiment shown in FIG. 1, the x-ray diagnostic device for implementation of the inventive method is a computed tomography apparatus 1. The computed tomography apparatus 1 has a gantry 2 with a rotary frame 3 arranged in the gantry 2 that is rotatable around a system axis Z of the computed tomography apparatus 1. An x-ray source 4 in the form of an x-ray tube is arranged on the rotary frame 3. From the focus F of the x-ray tube an x-ray beam 5 is emitted that is shaped with diaphragms (known but not shown in FIG. 1), for example to produce a fan shape or pyramid shape, so the focus F exhibits a fan or aperture angle β. In the exemplary embodiment a multi-line x-ray detector 6 is arranged opposite the x-ray source 4 on the rotary frame 3. Rotation of the rotary frame 3 is effected with an electrical drive 7 associated with the rotary frame 3.

The computed tomography apparatus 1 furthermore has a known patient positioning device (of which only a support plate 8 is shown in FIG. 1 for clarity) on which a patient P is supported who can be displaced in the direction of the system axis Z relative to the rotary frame 3.

To acquire image data for the patient P shown in FIG. 1, the patient P on the support plate 8 is moved into or through the opening 9 of the rotary frame 3. The patient P can be examined in a sequence mode or in a spiral mode with continuous feed of the support plate 8, with x-ray radiation 5 emanating from the focus F of the x-ray source 4 penetrating the body region of the patient P to be examined and striking the x-ray detector 6. The rotary frame 3 with the x-ray source 4 and the x-ray detector 6 rotates in the φ-direction around the system axis Z of the computed tomography apparatus 1, thus around the patient P. X-ray projections of the body region of the patient P thus are acquired from different projection directions. X-ray radiation that has been attenuated by passage through the patient P strikes the x-ray detector in each x-ray projection. The x-ray detector 6 thereby generates signals corresponding to the intensity of the incident x-ray radiation. From the signals determined with the x-ray detector 6, a computer 10 subsequently calculates (in a known manner) one or more two-dimensional or three-dimensional images of the body region of the patient P of whom the x-ray projections were acquired from different projection directions. The images can be shown on a monitor 11. An input unit such as the keyboard 12 and a computer mouse 13 shown as examples in FIG. 1 are provided for operation of the computed tomography apparatus 1.

Figure 2:
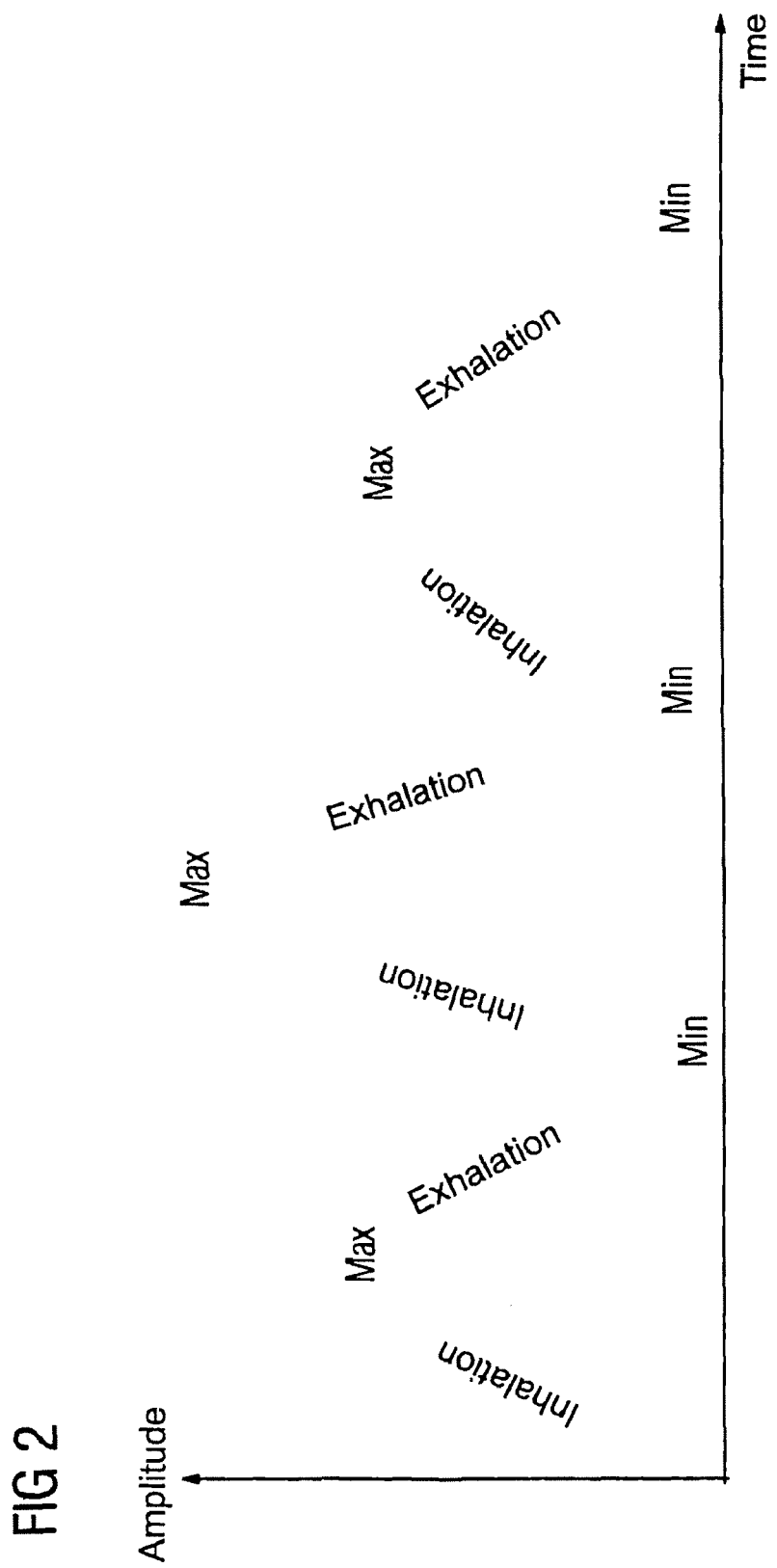
FIG. 2 is a curve of measured respiration signals with different amplitudes and lengths of the respiration cycle.

For continuous acquisition of respiration signals of the patient P, in the exemplary embodiment, the x-ray diagnostic device has a respiration belt 14 (which is an expandable belt) which, in the case of the preferred exemplary embodiment in FIG. 1, is schematically indicated around the chest of the patient P. A pressure sensor 15 is located in a pocket (not explicitly shown) of the respiration belt. By suitable arrangement of the pressure sensor 15 in the pocket and pre-stressings of the respiration belt 14, during respiration of the patient P the chest of the patient P expands and contracts so the pressure sensor 15 emits continuous signals that are supplied to a signal processing device 16. The signal processing device 16 prepares (for example amplifies) the signals if necessary and forwards them to the computer 10 of the computed tomography apparatus 1 for further evaluation. The signals forwarded to the computer 10 are designated in the following as respiration signals of the patient P and (as shown as an example in FIG. 2) can be displayed as a respiration curve on the viewing device 11. Three respiration cycles of the patient P are shown as examples in FIG. 2, with each respiration cycle being characterized by a phase of the inhalation and a phase of the exhalation. As can be seen from FIG. 2, the respiration cycles of the patient P are normally not identical, thus not absolutely periodical, but instead deviate from one another in their duration and in the level of the values of the amplitudes.

These variations of the respiration cycles of the patient P can lead to movement artifacts in the images given the acquisition of images of a body region of the patient P who executes a movement due to respiration. Furthermore, for the generation of images of a body region that moves due to the respiration of the patient P, it is frequently desirable to acquire the x-ray projections underlying the acquisition of the images in a respiration-triggered manner, i.e. dependent on the respiration of the patient P. The acquisition of x-ray projections of the lung is an example. Such x-ray projections can be acquired in phases of the inhalation or in phases of the exhalation, which under the circumstances can be relevant for the diagnostic following the image generation.

In order to expose the patient P to an optimally low dose of x-ray radiation given the generation of images of a body region that moves as a consequence of respiration, the intensity of the x-ray radiation emanating from the x-ray source 4 is modulated in the acquisition of the x-ray projections such that the intensity assumes a desired value or a value decreased relative to the desired value dependent on the values of the amplitudes of the respiration signals and/or the respiration position of the patient P. The intensity of the x-ray radiation should assume the desired value in the phase of the respiration cycle of the patient P in which x-ray projections of the body region of the patient P moving as a consequence of the respiration are acquired for generation of images of the body part of the patient P, and the intensity of the x-ray radiation should assume a value decreased relative to the desired value in the other phases that are normally not relevant for the imaging. For example, in the non-relevant phases of a respiration cycle the intensity of the x-ray radiation can be decreased to 20% of the intensity of the desired value. How high the desired value should be and to what extent the decrease should ensue is individually predeterminable for each patient via the input unit of the computed tomography apparatus 1.

Various examples for modulation of the intensity of the x-ray radiation are described in the following.

Figure 3:
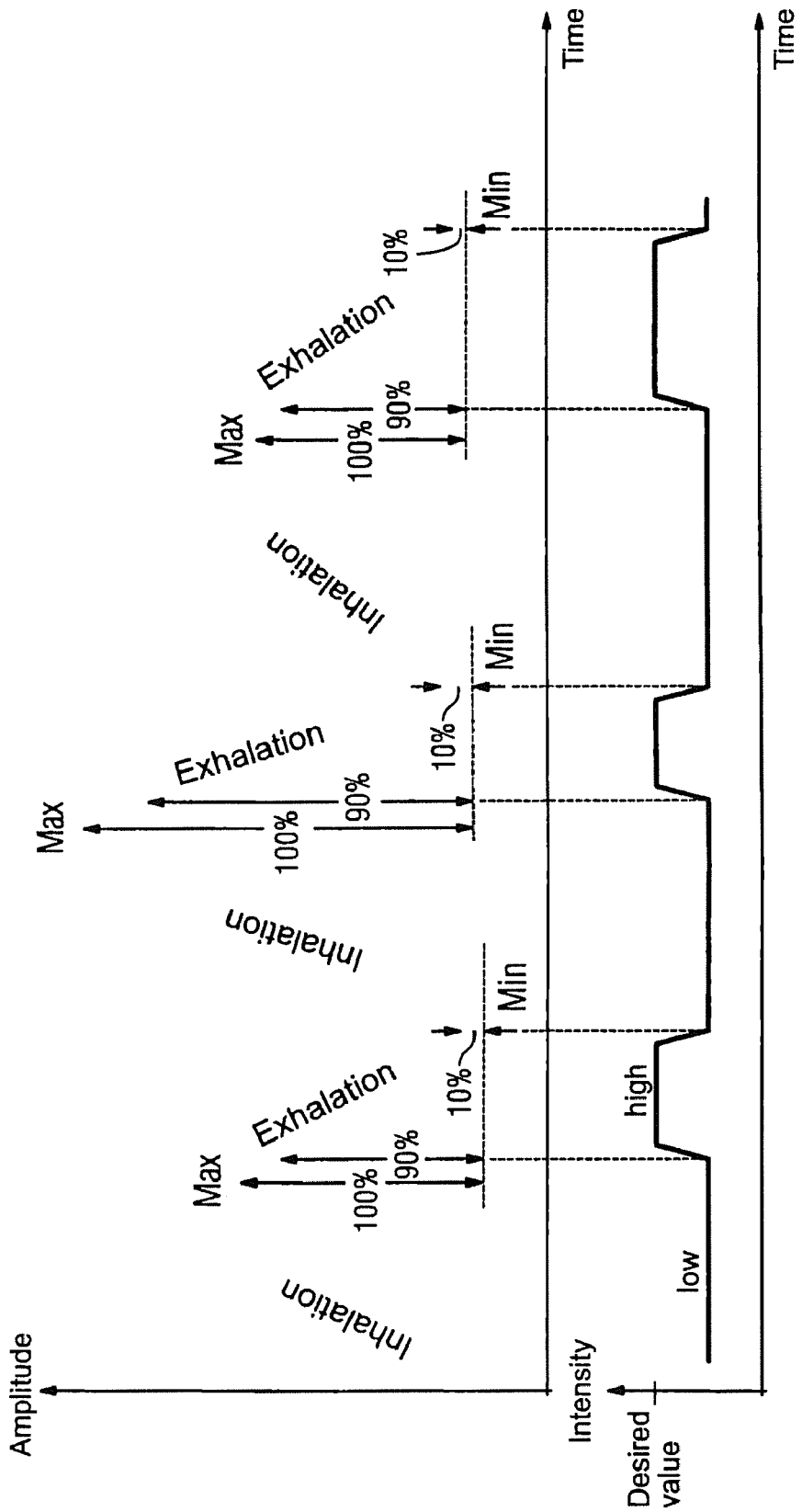
FIGS. 3 through 7 are diagrams for explaining execution of the inventive method.

As is illustrated using the three respiration cycles of the patient P shown in FIG. 3, x-ray projections of the body part of the patient P moving due to the respiration are presently acquired from different projection directions in the phase of the exhalation of the patient P. X-ray exposures of the body part of the patient P are acquired with high intensity when the ratio of the value of the current amplitude of the respiration cycle (measured with the respiration belt) to the last-measured amplitude maximum of the respiration cycle lies between 90% and 10%. If the ratio of the value of the amplitude of the currently-measured respiration signal to the last-measured amplitude maximum of the respiration cycle reaches the 90% mark, x-ray projections of the patient P are acquired with high intensity from different projection directions until the 10% mark is reached. Until reaching the next 90% mark during the exhalation of the patient P in the next respiration cycle, x-ray projections from different projection directions are subsequently acquired with a lower intensity that lies below the desired value. This procedure takes place until the x-ray projections required for reconstruction of an image are acquired. The modulation of the intensity of the x-ray radiation ensues such that, after specification of the respective limit values by means of the input unit (90% and 10% limit value given exhalation), the computer 10 of the computed tomography apparatus 1 continuously evaluates the respiration signals, sets them in relation to the last measured amplitude maximum, and activates a generator device 17 associated with the x-ray source dependent on the ratio. This can ensue, for example, such that the x-ray current of the x-ray tube 4 is correspondingly modulated. The method accordingly has the result that, in the acquisition of x-ray projections, the patient P is only exposed to x-ray radiation of an intensity that is necessary to generate x-ray images of high quality only in the phases of the respiration cycle that are relevant for the imaging. Generally, the range or the interval of the respiration cycle in which x-ray projections with high intensity are acquired is not selected too small, so that sufficient measurement data exists for the reconstruction of images of the body region of the patient P to be represented. For reasons of safety, in the phases of the respiration cycle that are not relevant for the imaging, the intensity of the x-ray radiation is not decreased to zero (which amounts to a deactivation of the x-ray source) so as to also acquire x-ray projections in those phases. If necessary, the projections acquired in these other phases thus are available for use as supplementary x-ray projections should the x-ray projections acquired in a phase of high intensity not be sufficient for the reconstruction of an image. In this case the resulting or reconstructed image will in fact not be an image of the highest quality. Nevertheless, an image can actually be reconstructed without having to conduct the entire measurement method again.

The computer 10 is, as already indicated, configured (i.e. provided with corresponding programs, program modules and routine) such that the inventive method can be executed with it. The phases in which x-ray projections are acquired with high intensity are determined based on the predetermined limit values, the desired value for the intensity, the decreased value for the intensity and the continuous evaluation of the currently-measured respiration signals. The generator unit 17, which generates operating currents and voltages for the x-ray source 4, is thereupon correspondingly controlled.

From FIG. 3 it can be seen that the acquisition of x-ray projections is adapted to the respective patient due to the inventive method. In spite of different respiration cycles, x-ray projections with high intensity of the x-ray radiation are always acquired in the phase of the exhalation between the 90% and 10% marks. Therefore the points in time at which x-ray projections with high intensity are acquired are not absolutely regular, and the duration of these phases of the acquisition of x-ray projections with high intensity is also variable dependent on the respective respiration cycle.

Figure 4:
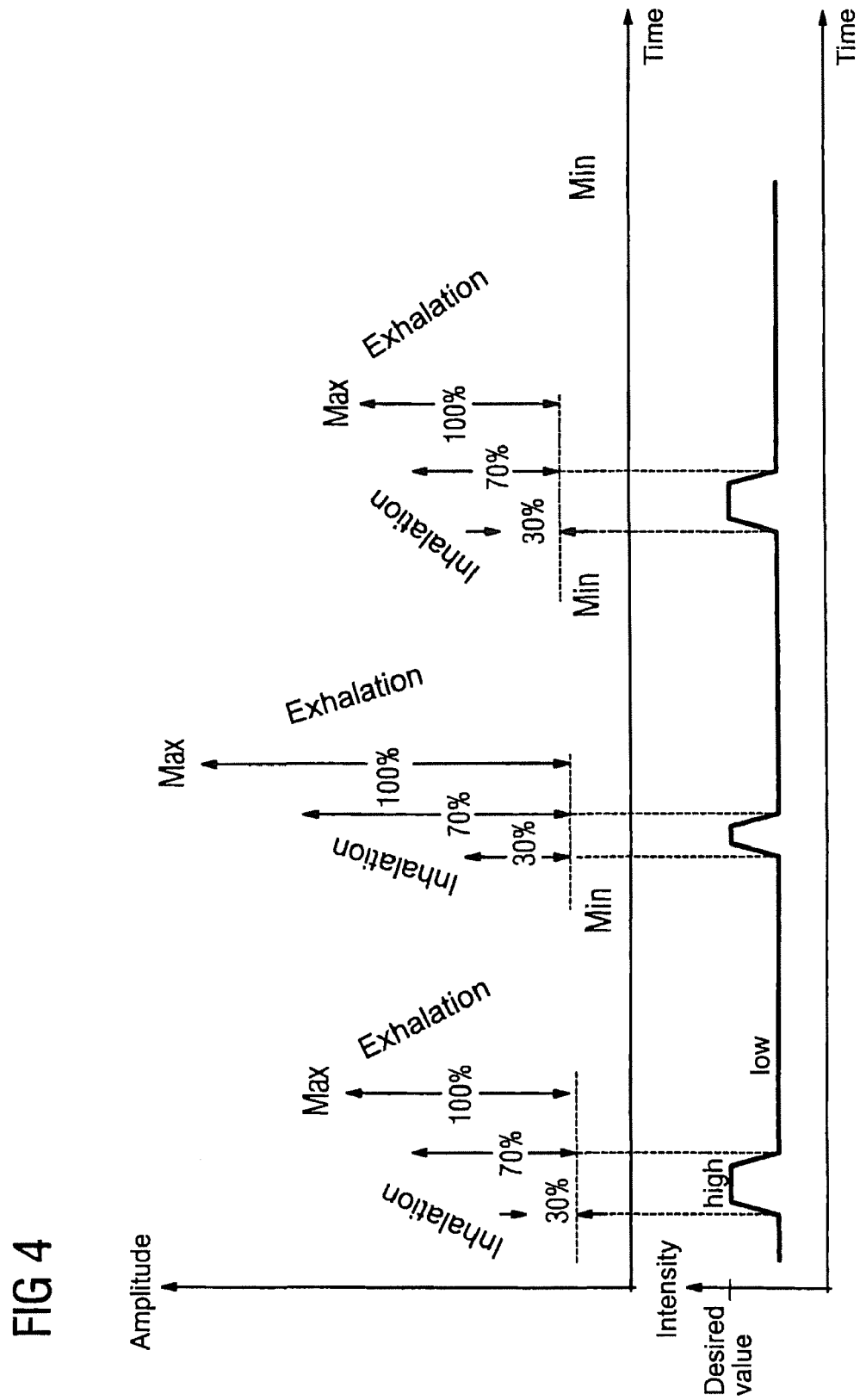

The acquisition of x-ray projections of a body part of the patient P (which body part moves as a consequence of respiration) during the phase of the inhalation of the patient P is illustrated as an example in FIG. 4 using three respiration cycles of the patient P. According to this, x-ray projections with high intensity are acquired when the ratio of the value of the amplitude of the currently-measured respiration signal of the patient P to the value of the last-measured amplitude maximum is greater than or equal to 30% or smaller than or equal to 70%. Since, in the case of the respiration cycles shown in FIG. 4 during the phase of the inhalation (thus at the point in time of a respiration cycle in which the maximum is not yet reached), this amplitude cannot be used for triggering of the acquisition of x-ray projections with high intensity, the maximum of the preceding respiration cycle must be used, which is disadvantageous under the circumstances. For this reason, in such a case it can be reasonable to use a comparison value that is based on measured amplitude maximums of a number of preceding respiration cycles as a reference variable. A suitable comparison value can be determined, for example, such that a number of amplitude maximums of a number of respiration cycles are averaged and the average value is used as a comparison value. Alternatively, a median filter can be applied in order to determine the comparison value from a number of amplitude maximums.

Figure 5:
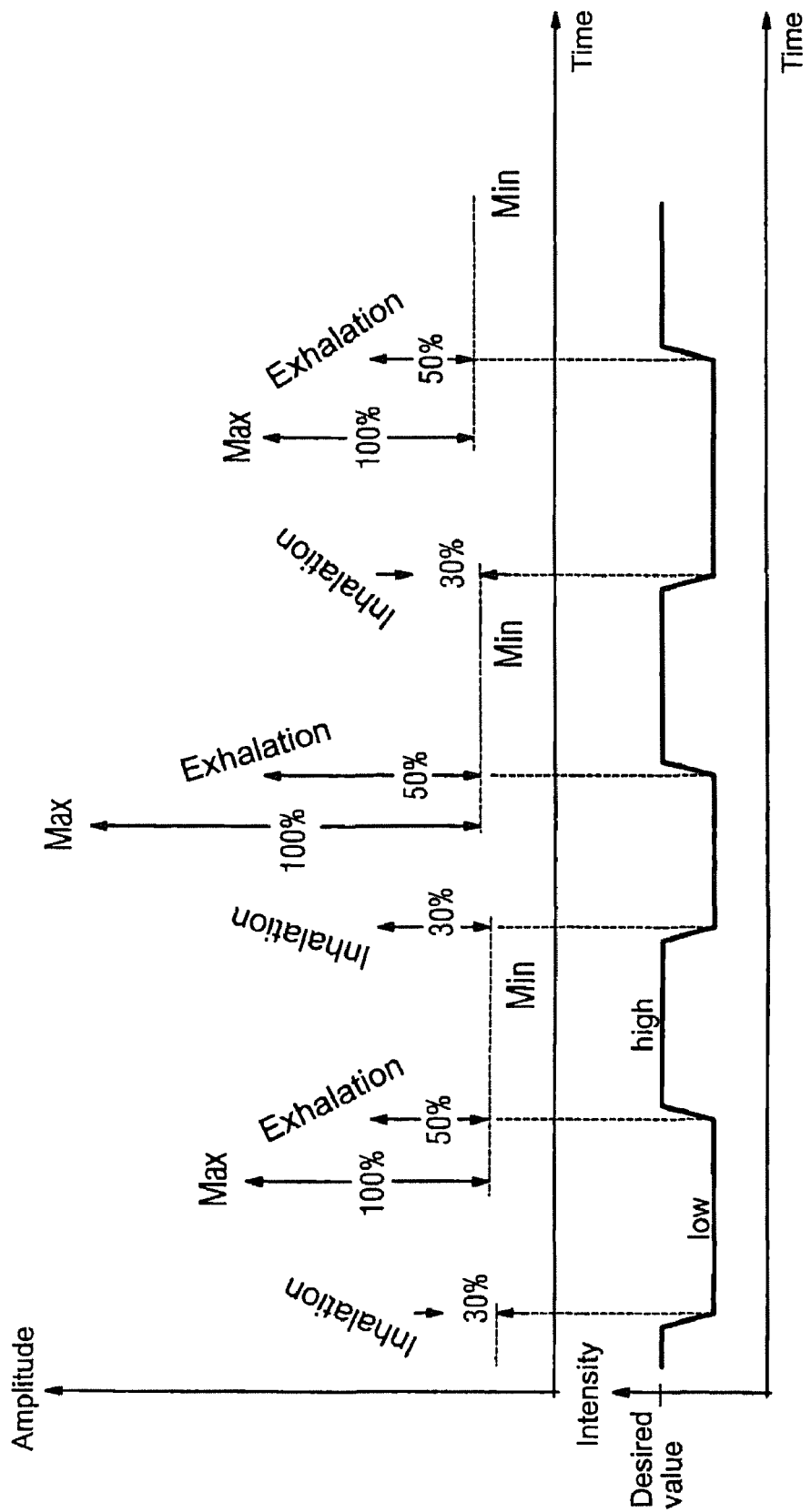

In FIG. 5 it is shown as a further variant that the acquisition of x-ray projections with high intensity can extend from the phase of the exhalation into the phase of the inhalation. It is shown in FIG. 5 that the acquisition of x-ray projections begins with high intensity when, in the phase of the exhalation of a first respiration cycle, the ratio of the value of the amplitude of a currently-measured respiration signal to the comparison value (which can be the value of the last-measured amplitude maximum or another determined comparison value) has reached 50%. The acquisition of x-ray projections with high intensity finally ends when, in the phase of the inhalation of the subsequent respiration cycle, the ratio of the value of the currently-measured respiration signal to the comparison value has reached 30%.

Figure 6:
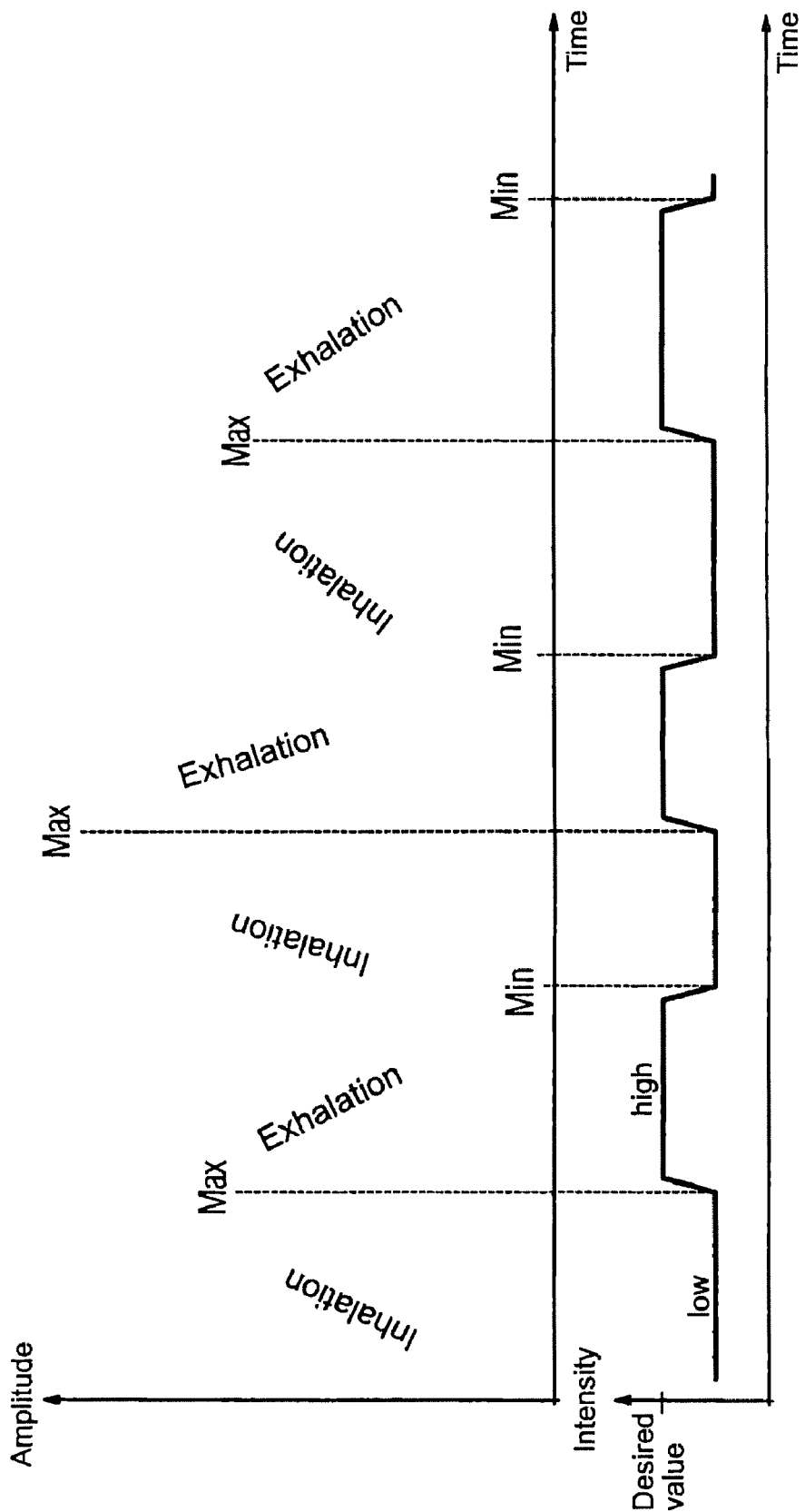

FIG. 6 shows that the acquisition of x-ray projections with high intensity can also ensue only in the phase of the exhalation. If the current maximum of the measured respiration signals is thus reached in a respiration cycle, the acquisition of x-ray projections of high intensity is begun, which acquisition ends when the respiration cycle ends (i.e. when the minimum of the measured respiration signals is reached). The acquisition of x-ray projections with high intensity can also ensue in the same manner during the phase of the inhalation. The modulation of the intensity thereby ensues when the maximum of the inhalation or the minimum of the exhalation is detected by the computer 10 using the measured respiration signals.

Figure 7:
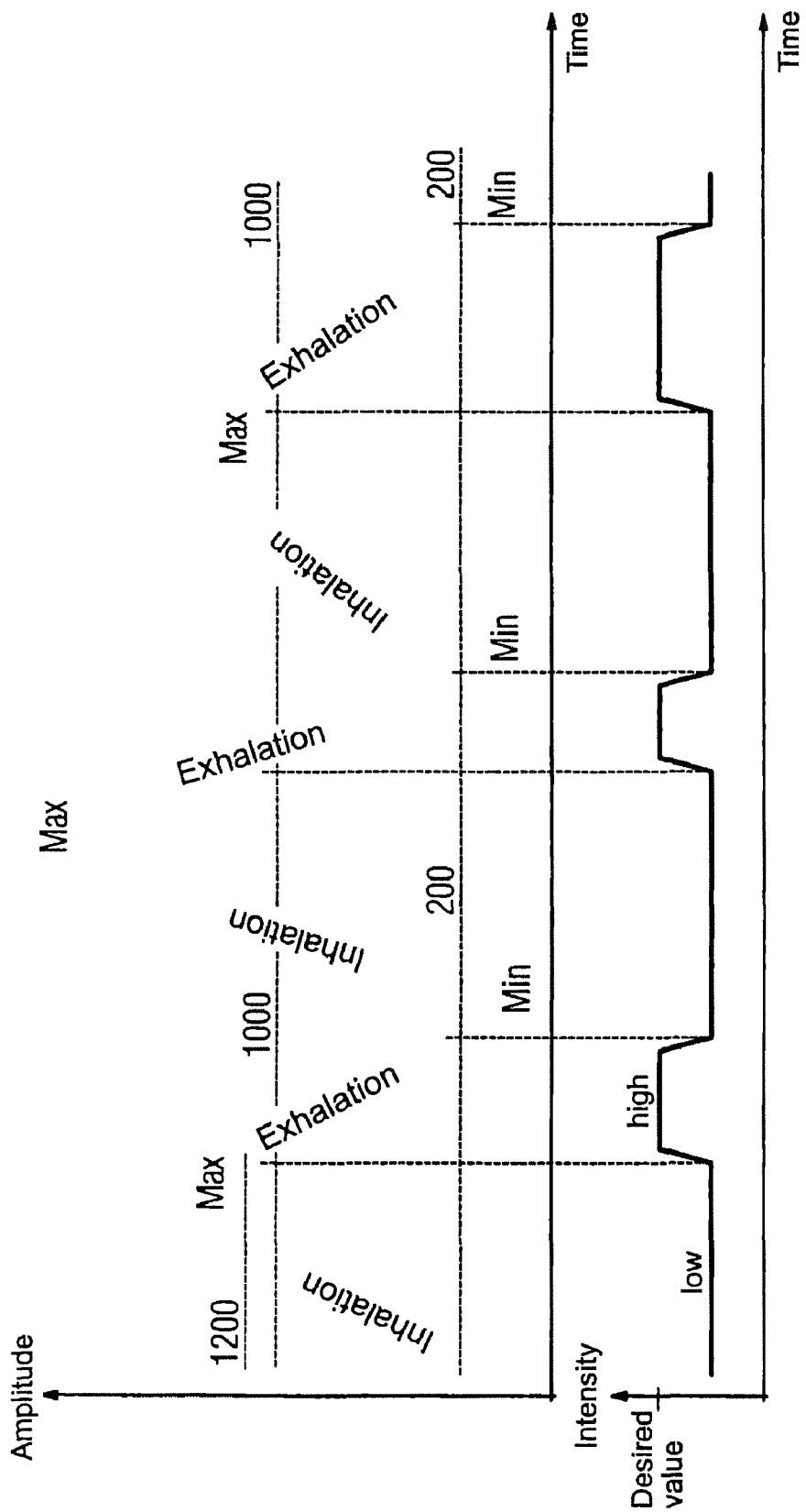

FIG. 7 shows that the acquisition of x-ray projections with high intensity can also be made dependent on absolute amplitude limit values adapted to the respective patient P, if applicable still dependent on the phase of the inhalation or the exhalation. In FIG. 7 it is thus shown that x-ray projections with high intensity are acquired in the phase of the exhalation when the absolute amplitude value falls below 1000 and the acquisitions with high intensity are ended when the amplitude value falls below 200.

Because the acquisition of x-ray projections of the patient P with high intensity is made dependent on the value of the amplitude of the currently-measured respiration signal and/or the respiration position of the patient P, the patient P is exposed overall to a lower x-ray dose in order to generate an image of a body region that executes a movement due to respiration. Moreover, by targeted selection of the acquisition regions of the x-ray projections with high intensity images with movement artifacts are prevented from being acquired. In this case, phases of the respiration cycle are selected in which a relatively slight movement of the body region to be shown in the image ensues as a consequence of the respiration. In particular given the acquisition of x-ray projections with high intensity in the spiral mode of the computed tomography apparatus, the method described above, offers the advantage that images of a body region of the patient P moving due to respiration are possible at practically any respiration phases and at any position of the patient P in the direction of the system axis Z. Overlapping reconstructions of the images thereby additionally lead to a significantly-improved 3D image quality. Due to the continuous table feed during the acquisition of the x-ray projections, the volume of the patient P to be mapped in images is clearly scanned [sampled] more quickly than in a sequentially-triggered mode. Due to the faster scanning of the volume, images of thinner body slices of the patient P can also be generated, which in turn results in a better resolution.

The method and the x-ray diagnostic device have been explained in the preceding based on the example of a computed tomography apparatus of the third generation, but computed tomography apparatuses of the fourth and fifth generations are also suitable for the method.

Alternatively, for acquisition of x-ray projections from different projection directions from which a 3D image is subsequently reconstructed, a C-arm x-ray apparatus can be used instead of the computed tomography apparatus, the x-ray source and x-ray detector (arranged on a C-arm) of which C-arm x-ray apparatus are moved around the body region to be acquired of the patient to acquire the x-ray projections from different projection directions. In this case, the acquisition of x-ray projections with high intensity can also be made dependent on the currently-measured value of the respiration signal of the patient in order to expose the patient to a lower x-ray dose overall in the acquisition of the x-ray projections.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an image of a body region of a living subject, said body region exhibiting movement due to respiration of the subject, said method comprising the steps of:

acquiring an electrical respiration signal from the subject that tracks said respiration of the subject, said respiration signal having a continuously changing amplitude;

emitting x-ray radiation into said body region, and detecting said x-ray radiation after passage through said body region, from a plurality of different projection directions, to acquire a plurality of x-ray projections of said body region, and modulating an intensity of said x-ray radiation from said x-ray source during acquisition of said x-ray projections to acquire one of said projections with said intensity set at a predetermined value at a time coinciding with a first value of said amplitude and, to acquire another of said x-ray projections with said intensity set at a value that is decreased relative to said predetermined value, at a time coinciding with a second value of the amplitude of said respiration signal; and reconstructing an image of said body region of the subject from x-ray projections in said plurality of said x-ray projections that include said one of said x-ray projections and said another of said x-ray projections.

2. A method as claimed in claim 1 comprising setting said intensity of said x-ray radiation to said predetermined value when a ratio of the amplitude of a currently-obtained respiration signal to a last-obtained maximum of said amplitude is greater than or equal to a predetermined limit value.

3. A method as claimed in claim 1 comprising setting said intensity of said x-ray radiation to said predetermined value when a ratio of the amplitude of a currently-obtained respiration signal to a last-obtained maximum of the amplitude is less than or equal to a predetermined limit value.

4. A method as claimed in claim 1 comprising generating a comparison value from a plurality of maxima of said amplitude for a plurality of respiration cycles of said respiration of the subject, and setting the intensity of the x-ray radiation to said predetermined value when a ratio of the amplitude of a currently-obtained respiration signal to said comparison value is greater than or equal to a predetermined limit value.

5. A method as claimed in claim 1 comprising generating a comparison value from a plurality of maxima of said amplitude for a plurality of respiration cycles of said respiration of the subject, and setting the intensity of the x-ray radiation to said predetermined value when a ratio of the amplitude of a currently-obtained respiration signal to said comparison value is less than or equal to a predetermined limit value.

6. A method as claimed in claim 1 comprising setting the intensity of the x-ray radiation to said predetermined value only during a respiration phase, represented by said respiration signal, selected from the group consisting of inhalation and exhalation.

7. A method as claimed in claim 6 comprising determining a comparison value from respective maxima of said amplitude in a plurality of respiration cycles of said respiration of said subject, and setting the intensity of the x-ray radiation to said predetermined value in said phase when a ratio of the amplitude of a currently-obtained respiration signal to a last-obtained maximum of the amplitude or to said comparison value is less than or equal to a first predetermined limit value and greater than or equal to a second predetermined limit value.

8. A method as claimed in claim 6 comprising determining a comparison value from respective maxima of said amplitude in a plurality of respiration cycles of said respiration of said subject, and setting the intensity of the x-ray radiation to said predetermined value in said phase when a ratio of the amplitude of a currently-obtained respiration signal to a last-obtained maximum of the amplitude or to said comparison value is greater than or equal to a first predetermined limit value and less than or equal to a second predetermined limit value.

9. A method as claimed in claim 1 comprising setting the intensity of the x-ray radiation to said predetermined value when the amplitude of a currently-obtained respiration signal is between a lower amplitude limit value and an upper amplitude limit value.

10. A method as claimed in claim 9 comprising establishing said lower amplitude limit value and said upper amplitude value using amplitudes in previously-obtained respiration signals from said subject.

11. A method as claimed in claim 9 comprising setting the intensity of the x-ray radiation to said predetermined value only during a phase of said respiration, represented by said respiration signal, selected from the group consisting of inhalation and exhalation.

12. A method as claimed in claim 1 comprising continuously acquiring said respiration signal from said subject.

13. A method as claimed in claim 1 comprising acquiring said plurality of x-ray projections with an x-ray computed tomography apparatus.

14. A method as claimed in claim 1 comprising acquiring said plurality of x-ray projections by continuously rotating said x-ray source and an associate radiation detector that detects said x-ray radiation after passage through said subject, around said subject.

15. A method as claimed in claim 1 comprising acquiring said plurality of x-ray projections using a C-arm x-ray apparatus.

16. A method as claimed in claim 1 comprising selecting said first value of said amplitude to represent a phase of said respiration subject that is desired to be depicted in said image of said body region.

17. An x-ray diagnostic apparatus for generating an image of a body region of a living subject, said body region exhibiting movement due to respiration of the subject, comprising:

a respiration monitor that acquires an electrical respiration signal from the subject that tracks said respiration of the subject, said respiration signal having a continuously changing amplitude;

an x-ray apparatus having an x-ray source that emits x-ray radiation into said body region, and a radiation detector that detects said x-ray radiation after passage through said body region, from a plurality of different projection directions, to acquire a plurality of x-ray projections of said body region, and a control arrangement connected to said respiration detector and to said x-ray source that modulates an intensity of said x-ray radiation from said x-ray source during acquisition of said x-ray projections by setting said intensity at a predetermined value to acquire one of said x-ray projections at a time coinciding with a first value of said amplitude and by setting said intensity at a value that is decreased relative to said predetermined value to acquire another of said x-ray projections at a time coinciding with a second value of the amplitude of said respiration signal; and an image reconstruction computer that reconstructs an image of said body region of the subject from x-ray projections in said plurality of said x-ray projections that include said one of said x-ray projections and said another of said x-ray projections.

18. An x-ray diagnostic apparatus as claimed in claim 17 comprising an input unit allowing manual entry, into said control arrangement, of said predetermined value of the intensity and said value of the intensity that is decreased relative to said predetermined value.

19. An x-ray diagnostic apparatus as claimed in claim 17 wherein said x-ray apparatus is a computed tomography data acquisition apparatus.

20. An x-ray diagnostic apparatus as claimed in claim 17 wherein said x-ray apparatus is a C-arm x-ray apparatus.

21. An x-ray diagnostic apparatus as claimed in claim 17 wherein said control arrangement selects said first value of said amplitude to represent a phase of said respiration of said subject that is desired to be depicted in said image of said body region.

* * * * *